US006468733B2

(12) United States Patent
Nur et al.

(10) Patent No.: US 6,468,733 B2
(45) Date of Patent: Oct. 22, 2002

(54) METHOD OF THE INACTIVATION OF VIRUSES BY A SOLVENT-DETERGENT COMBINATION AND NANOFILTRATION

(75) Inventors: Israel Nur, Moshav Timurim; Liliana Bar, Rehovot, both of (IL)

(73) Assignee: Omrix Biopharmaceuticals Inc., Fairfax, VA (US)

( * ) Notice: Subject to any disclaimer, the term of this patent is extended or adjusted under 35 U.S.C. 154(b) by 0 days.

(21) Appl. No.: 09/843,153

(22) Filed: Apr. 27, 2001

(65) Prior Publication Data

US 2002/0009707 A1 Jan. 24, 2002

(30) Foreign Application Priority Data

Jun. 5, 2000 (IL) ................................................ 136552

(51) Int. Cl.$^7$ ................................................ A01N 1/02
(52) U.S. Cl. ........................... 435/2; 435/180; 424/530; 210/656; 530/387.1; 530/412; 530/414; 530/415; 530/417; 530/418; 530/422
(58) Field of Search ...................... 435/2, 180; 424/530; 210/656; 530/387.1, 412, 414, 415, 417, 418, 422

(56) References Cited

U.S. PATENT DOCUMENTS

| 4,789,545 A | 12/1988 | Woods et al. |
| 5,094,960 A | 3/1992 | Bonomo |
| 5,486,293 A | 1/1996 | Boschetti et al. |
| 5,648,472 A | 7/1997 | Gehringer et al. |

FOREIGN PATENT DOCUMENTS

| EP | 0 131 740 | 9/1994 |

OTHER PUBLICATIONS

Burnouf–Radosevich et al., "Nanofiltration, a New Specific Virus Elimination Method Applied to High–Purity Factor IX and Factor XI Concentrates", *Vox Sanquinis*,1994, p. 132–138, vol. 67, No. 2.

Burnouf et al., "Reducing the Risk of Infection from Plasma Products: Specific Preventative Strategies", *Blood Reviews*, 2000, p. 94–110, vol. 14.

Guerrier, "Specific Sorbent to Remove Solvent–Detergent Mixtures from Virus–Inactivated Biological Fluids", *Journal of Chromatography B*, 1995, p. 119–125, vol. 664.

Stucki et al., "Characterisation of a Chromatographically Produced Anti–D Immunoglobulin Product", *Journal of Chromatography B*, 1997, p. 241–248, vol. 700.

Troccoli et al., "Removal of Viruses from Human Intravenous Immune Globulin by 35 nm Nanofiltration", *Biologicals*, 1998, p. 321–329, vol. 26.

*Primary Examiner*—Jeffrey Stucker
(74) *Attorney, Agent, or Firm*—Browdy and Neimark, P.L.L.C.

(57) ABSTRACT

The invention concerns a method for elimination of viruses from a biological preparation wherein initially enveloped viruses are eliminated by a solvent-detergent step, then the solvent-detergents are removed by a resin composed of silicon beads and finally the preparation is nanofiltered.

10 Claims, 2 Drawing Sheets

METHOD OF THE INACTIVATION OF VIRUSES BY A SOLVENT-DETERGENT COMBINATION AND NANOFILTRATION

FIELD OF THE INVENTION

The present invention concerns a method for the removal and inactivation of viruses from biological preparations.

BACKGROUND OF THE INVENTION

Biologically derived liquid preparations such as blood and plasma preparations are used as raw materials from which a plurality of biologically useful compounds can be purified. Examples of such compounds include immunoglobulin, factor VIII, albumin, α 1 anti trypsine, Factor IX, factor XI, PPSB, fibrinogen, and thrombin (prothrombin). In addition, various biological products such as hormones, growth factors, enzymes and ligands are isolated from biological preparations obtained from cell cultures.

The cells used in the production of these useful materials may be either wild-type cells from various animal sources, or alternatively, genetically engineered prokaryotic or eukaryotic cells. Where the biological materials obtained from these liquid preparations are to be administered to humans for therapeutic purposes, in particular by intravenous administration, the sterility of the preparation is of major concern. Thus, great efforts are invested in the inactivation of viruses, such as hepatitis viruses and HIV viruses, which may be present in these preparations.

Lipid coated viruses are effectively inactivated by treatment with non-ionic biocompatible solvents and detergents. Methods for virus inactivation by solvent-detergent applications are described, for example, in EP 0131740. However, non-lipid coated viruses cannot be inactivated by solvent-detergent treatments, thus, other inactivation methodologies have to be used for their inactivation. These include the application of heat (pasteurization), the application of irradiation such as short ultra violet light (UVC) or gamma radiation, as well as eliminating by physical means, e.g., the filtration of the preparation through very narrow filter holes so as to remove viruses by size exclusion (nanofiltration).

Noreen et al., (*Biologicals*, 26:321–329 1998) examines the use of the Memberg Microporous membrane hollow fibers (Planova) 35 mn filters to reduce potential loads of both non-enveloped and enveloped viruses, prior to the solvent detergent treatment in a 7% IVIg solution. In the above study, nanofiltration was validated for the removal of a variety of enveloped and non-enveloped viruses ranging in size from 70 nm to 18 nm including: Sindbis virus, Simian Virus 40 (SV40), Bovine Viral Diarrhea virus (BVDV), Feline calicivirus, Encephalomyocarditis virus (EMC), Hepatitis A virus (HAV), Bovine Parvovirus (BPV) and Porcine Parvovirus (PPV). The study showed a complete reduction (to the limit of detection assay) of all viruses larger than 35 nm. Interestingly, even smaller viruses such as EMC and HAV were at least partially removed by this method of filtration.

These studies led to the use of nanofiltration for the removal of viruses from biological preparations. However, in cases where it was desired to combine both viral inactivation by the solvent-detergent method, (in order to inactivate lipid-coated viruses) as well as nanofiltration elimination (for the size exclusion and hence removal of non-lipid coated viruses), it was discovered that the nanofiltration step had to proceed the solvent-detergent application, particularly, where the solvent-detergent was to be removed by oil extraction and C-18 reverse phase resin. The reason for this was that after extraction of the solvent-detergent, there are always traces of small oil droplets, as well as residues of solvent-detergent, which bind to the hydrophilic part of the resin. Moreover, some of the proteins purified from the biological preparation may be modified during the purification process, and the altered proteins can form dimers and polymers which change in the hydrophobicity of the altered protein. These traces of oil droplets, protein dimer aggregates and the mixture of oil and protein residues tend to block the small holes of the nanofilter, thus considerably increasing the time of the filtration, requiring the frequent replacement of expensive filters, and generally decreasing the yield of the product.

The residues of oil droplets (contaminants), which tend to block nanofilters, were removed by using either a chromatography mechanism of molecular exclusion or by hydrophobic chromatography. However, none of the conventional methods for the removal of solvent detergent has yet addressed the issue of dimerization or aggregation caused by the solvent detergent, and this problem still remains. Removal of the solvent-detergents from biological liquid preparations, such as immunoglobulin preparations, is generally carried out by using gel chromatography. U.S. Pat. No. 5,094,960 and U.S. Pat. No. 5,648,472 concern the removal of solvent-detergent from immunoglobulin preparations without using gel reverse phase (hydrophobic) chromatography.

Two other patents have been granted to processes which indicate that the removal of solvent detergent affects the stability of a liquid IVIg product (U.S. Pat. No. 5,094,960, U.S. Pat. No. 4,789,545 and U.S. Pat. No. 5,648,472). G. Werner and P. Selosse (U.S. Pat. No. 5,648,472) describe a process for preparing envelope virus-inactivated immunoglobulin solutions suitable for intravenous application, comprising treating the immunoglobulin with TnBP and/or Tritonx100™ (octylphenol ethylene oxide condensate; CAS 9002-93-1), followed by an extraction using biologically compatible vegetable oil, when TnBP and/or Tritonx100™ and vegetable oil are subsequently removed by solid-phase extraction on hydrophobic materials. This indicated that the combination of vegetable oil extraction of IVIg followed by chromatography through a hydrophobic column produces a very stable liquid solution of immunoglobulins, even at elevated temperature. This patent claimed that IVIg preparation is prepared in accordance to two previous patents:

Bonomo, 1992, (U.S. Pat. No. 5094960) teaches the use of solid phase extraction and Bulk C-18 packing from Waters, Inc. as a preferred resin. Woods 1986 (U.S. Pat. No. 4,789,545), features the removal of solvent detergent by naturally occurring oils, however the products obtained by this method resulted in the unstable preparation of intravenous immunoglobulins.

Guerrier et al (*Journal of Chromatography B* 664:119–125 (1995)) describes a specific sorbent which is intended to remove solvent-detergent mixtures from virus-inactivated biological fluids. The solvent-detergent removal (SDR) HyperD™ sorbents were supplied by Biosepra (Ceroy-Saint-Christophe, France). This chromatographic packing was made of silica beads in which the pore volume was filled with a three-dimensional cross-linked hydrophobic acrylic polymer.

SUMMARY OF THE INVENTION

The present invention is based on the finding that a method for the inactivation of viruses present in biological preparations comprising first treating the preparation by solvent-detergent, after which the solvent-detergent is extracted by the use of vegetable oil, in a combination with/without solid phase extraction (specifically using bulk C18 as recommended by U.S. Pat. No. 5,648,472) resulted in an immunoglobulin liquid preparation which was very difficult to pass through the Planova ™Filter 35 nm. Thus, it was realized that such a procedure was unsuitable for the efficient inactivation of viruses.

In accordance with the present invention, it was surprisingly discovered that the combination of solvent-detergent treatment, followed by chromatography utilizing SDR HyperD™ (ion-exchange resin) from Biosepra, facilitated the passage of the IVIg at a high flow rate through Planova Filters 35 nm, and resulted in a liquid preparation devoid of active viruses, while featuring a very high yield. In accordance with the present invention, it was further found that the problem of dimerization of immunoglobulins can be partially solved by reducing the pH to 4.0 before the nanofiltration step.

Thus, the present invention concerns a method for the inactivation of viruses present in a liquid preparation, comprising the steps of:

(i) contacting the biological liquid preparation with a solvent-detergent combination at concentrations and under conditions which are sufficient to inactivate lipid-coated viruses;

(ii) removing solvent-detergent traces from the liquid preparation by passing the liquid preparation obtained in (a), on a chromatographic packing composed of silica beads whose pore volume is filled with three-dimensional cross-linked hydrophobic acrylic polymer; and (iii) passing the liquid product of step (b) through a filter having a pore size ranging from about 15 nm to approximately 70 nm.

Optionally, after step (a) comes a step of extraction of the solvent-detergent by a hydrophobic composition such as oil, for example, a biologically compatible vegetable oil. The removal of the chromatographic packing in step (b) is thus also useful in the elimination of the oil traces and oil related impurities.

The term "*inactivating viruses*" refers both to the situation wherein viruses are maintained in the solution but are rendered non-viable (for example, by dissolving their lipid coat), as well as to the physical removal of the viruses from the liquid preparation (for example, by size exclusion). Thus, in the context of the invention, this term refers both to viral destruction and viral removal.

The term "*biological liquid preparation*" refers to any type of liquid preparation obtained from a biological source. This typically includes preparations obtained from body fluids such as blood, plasma and urine, as well as liquids obtained from cell cultures, containing biological substances secreted by the cells into the preparation, or containing substances which originally were present inside the cells, and were released to the liquid preparation due to various manipulations such as the lysing of the cells.

The method of virus inactivation, in accordance with the invention, may be used for a plurality of utilizations such as: the isolation of various proteins including immunoglobulins, factor VIII, albumin, α 1 anti trypsine, Factor IX, factor XI, PPSB, fibrinogen, and thrombin (prothrombin) and others; the isolation of genetically engineered proteins from cell cultures, the isolation of hormones, growth factors, enzymes, clotting factors, receptors, and other biologically active copolymers and the like.

In accordance with a preferred embodiment of the invention, the biological liquid preparation is intended for the isolation of immunoglobulins which are to be purified therefrom and is obtained by resuspending Paste II, from plasma fractionation, in water, adjusting the pH of the preparation and ultrafiltering and diafiltering the resulting products by using membrane filters to give a desired protein concentration.

The solvent-detergent combination used to deactivate lipid coated viruses may be any solvent-detergent combination known in the art such as TnBP and Triton X-100™, Tween 80™ (CAS 9005-65-6; polyoxyethylene sorbitan monooleate) and Sodium cholate and others. The concentration of the solvent detergents should be those commonly used in the art, for example, >0.1% TnBP and >0.1% Triton X-100™. Typically, the conditions under which the solvent-detergent inactivates the viruses consist of 10–100 mg/ml of solvent detergent at a pH level ranging from 5–8, and a temperature ranging from 2–37° C. for 30 min. to 24 hours. However, other solvent detergent combinations and suitable conditions will be apparent to any person versed in the art.

After undergoing solvent-detergent treatment, the bulk of the solvent-detergent is removed by the use of an SDR resin (solvent-detergent removal), which is a chromatographic packing made of silica beads in which the pore volume is filled with a three-dimensional cross-linked hydrophobic acrylic polymer. An example of such an SDR is the HyperD™ resin supplied by Biosepra.

The resulting preparation is then passed through a nanofilter, having a pore size of less than 70 nm, preferably between 15 and 50 nm. The precise size of the pore should be determined in accordance with the protein which has to be maintained in the liquid preparation, and the size of the viruses which have to be eliminated by size exclusion.

The method of the present invention has the following advantages over other methods of inactivation of viruses in which the nanofiltration step precedes the treatment with a solvent detergent:

(1) The amount of viruses which adhere to the pores of the filter is smaller (since some of the viruses were eliminated by the solvent-detergent treatment) so that the replacement of filters, which is an expensive part of the operation, is decreased.

(2) The time course of the procedure is decreased, since the liquid preparation, after being treated with the solvent-detergent and the SDR extraction, passes much more quickly through the nanofilter than had this nanofiltration step had been carried out as the first step of the method.

(3) Blocking the filters during the production resulted usually in a significant decrease in yield. The yield of the present invention is about 97–100%.

(4) The hydrophobic filling of the SDR resin decreases the dimer's concentration in the immunoglobulin solution. Once the immunoglobulin is depleted of its dimers, the low pH levels reduce the rate of new dimer formation by charging the molecules with additional negative charge which repels then from each other.

The dimerization problem where the preparation is an immunoglobulin preparation is solved partially by reducing the pH level to a pH below 5.

DETAILED DESCRIPTION OF THE INVENTION

Example 1: Inactivation of Viruses in Immunoglobulin Preparation

Paste II prepared from plasma by the Cohn fractionation method was resuspended in water for 18 hours; the pH was adjusted to 4.6 by the addition of HCl. The resulting solution was ultrafiltered/diafiltered by using 30,000 K Filtron membrane filters to give a protein concentration of 90 mg/ml. The pH was adjusted to 5.3 and 0.3% of TnBP and 1% Triton-100™ were added to the solution. The resulted suspension was incubated at 6° C. for 4 hours. The suspension was then split into two sub-processes. One suspension was first extracted by ricine oil followed by chromatography on a Bulk C-18 resin from Waters, and the second sample underwent (without prior oil extraction) chromatography on a Biosepra SDR HyperD™ resin.

Figure 1:
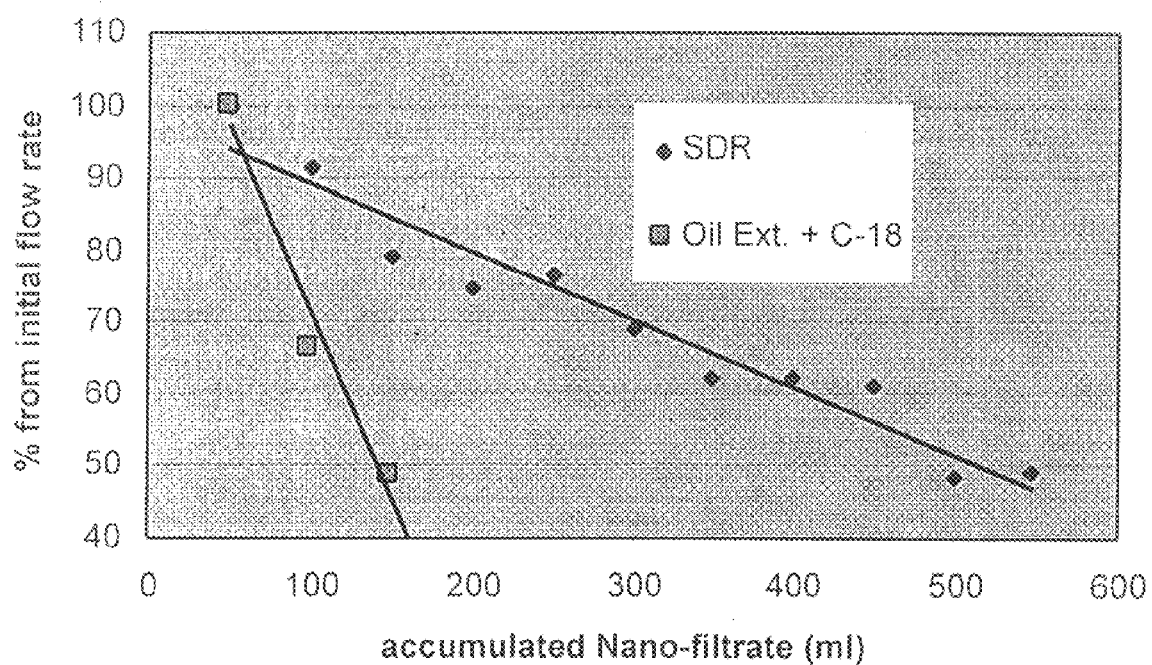
FIG. 1: shows the rate of nanofilter blocking, by presenting the reduction of flow rate as a function of the accumulated filtrate running through the nanofilter. Two sources of 45 mg/ml immunoglobulin solutions are used in this experiment: an IVIg solution in which the solvent detergent was removed by oil extraction followed by chromatography on C-18 and an IVIg solution in which the solvent detergent was removed by SDR alone.

Three hundred ml of each of the solutions were then filtered throughout a 0.2 μ cellulose acetate filter. Both solutions were then tested for their ability to pass a 35N Planova filter. The testing was designed as indicated in FIG. 1.

300–350 ml of protein solution is placed in a pressurized container. The pressure is supplied by a large reservoir of pressured nitrogen gas. This reservoir was filled as needed from a nitrogen cylinder. By increasing the pressure in the pressurized container the protein solution was flowing throughout a set of pre-filters of 0.2 μ, 0.1 μ followed by a Planova™ pre-filter of 75N.

The Planova™ 35N was connected at the end of the filter set which was also connected to a pressure gauge. The pressure was kept constant, at 10 PSI, on the 35N filter and 11–12 PSI on the 75N filter. Therefore under this constant pressure, if a partial blockage of the filter occurred, the flow rate of the protein solution throughout the filter decreases rapidly. The pressures before the two Planova™ filters (75N and 35N) were monitored during the entire filtration. The flow rate however was averaged for every 50 ml of solution passing the 35N filter. The filtration was stopped when the average flow rate reached a level lower than 50% of the initial flow rate. This kind of threshold represents the rate at which 50% of the filter holes are blocked. As can be seen from FIG. 1, the rate for this kind of solution is somewhat linear whereas measurement after this threshold is somewhat erroneous.

TABLE 1

Effect of C-18 resin as the SD removal procedure on the flow rates and pressures during nano-filtration in Example 1

| Measurement | Pressure (psi) before filter | | Flow rate | Filtration volume |
|---|---|---|---|---|
| | 75N | 35N | (ml/min) | (ml) |
| 1 | 12.5 | 10 | 0.91 | 50 |
| 2 | 12.5 | 10 | 0.6 | 50 |
| 3 | 12 | 10 | 0.44 | 50 |

TABLE 2

Effect of SDR resin as the SD removal procedure on the flow rates and pressures during nano-filtration in Experiment 1

| Measurement | Pressure (psi) before filter | | Flow rate | Filtration volume |
|---|---|---|---|---|
| | 75N | 35N | (ml/min) | (ml) |
| 1 | 11.5 | 10 | 1.16 | 50 |
| 2 | 12 | 10.3 | 1.06 | 50 |
| 3 | 12 | 10.5 | 0.92 | 50 |
| 4 | 12 | 10.8 | 0.87 | 50 |
| 5 | 12 | 10.8 | 0.89 | 50 |
| 6 | 12.5 | 11 | 0.8 | 50 |
| 7 | 12 | 11 | 0.72 | 50 |
| 8 | 12.5 | 10.9 | | 50 |
| 9 | 12.5 | 10.9 | 0.71 | 50 |
| 10 | 11 | 12.5 | 0.56 | 50 |
| 11 | 12 | 11 | 0.57 | 46 |

As shown in Tables 1 and 2 the initial flow rates were lower when using the C-18 resin (0.9 versus 1.16 ml/min.). Moreover, the flow rate decreased faster and as a consequence the filtration volume was lower when using the C-18 resin in comparison with SDR.

Figure 2:
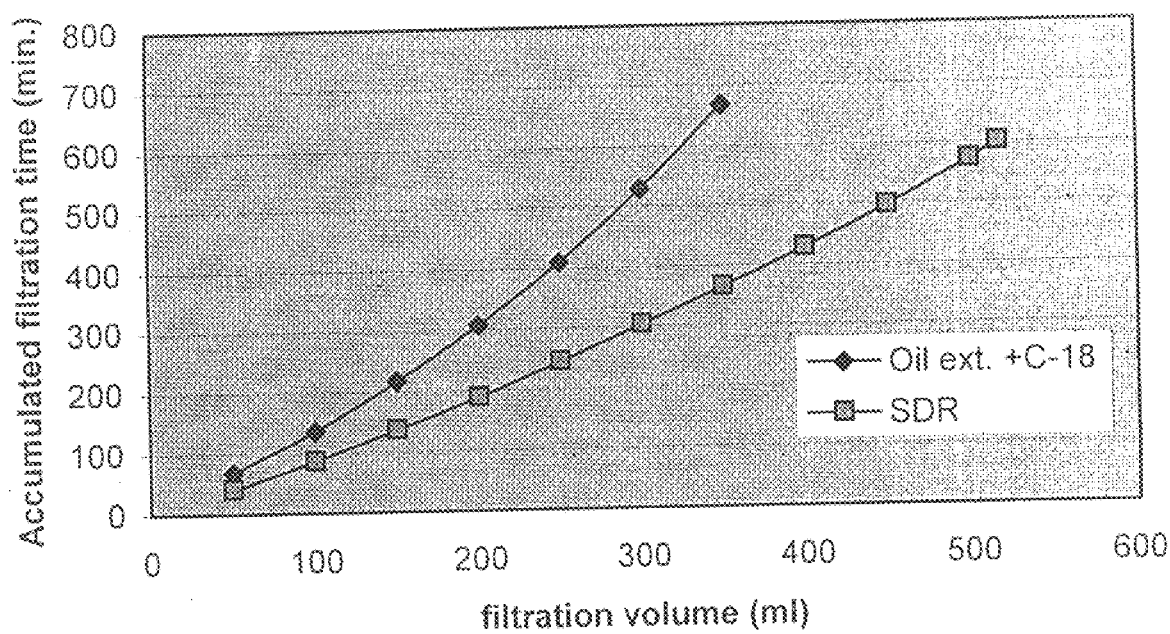
FIG. 2: shows the effect of solvent removal on the accumulated filtration time through a 35 N nanofilter; at elevated temperature (37° C.) the flow rate is somewhat faster in both methods for solvent detergent removal.

As can be seen in FIG. 2 and Tables 3–4 the amount of filtrate accumulate until the 50% threshold is reached, is at least twice faster and the volume is twice higher in the product which underwent chromatography by SDR than in the product where the S/D was removed by oil extraction followed by C-18 chromatography.

This is due to the removal of dimers, polymers and aggregates from the IgG solution by the SDR column chromatography.

In a laboratory scaled experiment, different conditions for the SD step were studied: the pH, S/D concentrations, temperature and incubation time length were chanted and the samples were chromatographed in SDR-columns. The following (Table 3) shows the averaged values of four replicates of the percentages of monomers, dimers and aggregates in IgG samples before and after SDR at the different conditions.

The results show a significant decrease of dimers and a very slight increase of aggregates (polymers) after the SDR column. The increase in aggregates (polymers) are with the standard error or analytical assay, independently of the SD conditions used.

TABLE 3

Effect of different S/D conditions on the molecular weight distribution of IgG solutions after SDR-chromatography

| Experimental conditions | | Before S/D addition and SDR | After 4.5 hs S/D Incubation and SDR |
|---|---|---|---|
| Production results | Monomers | 95.45 | 99.27 |
| | Dimers | 3.76 | 0.64 |
| | Polymers | 0.04 | 0.09 |
| Production conditions | Monomers | 96.17 | 99.25 |
| | Dimers | 3.78 | 0.61 |
| | Polymers | 0.04 | 0.15 |
| High pH | Monomers | 95.58 | 99.21 |
| | Dimers | 4.39 | 0.69 |
| | Polymers | 0.04 | 014 |
| Low pH | Monomers | 96.77 | 99.24 |
| | Dimers | 3.20 | 0.69 |
| | Polymers | 0.03 | 0.08 |

TABLE 3-continued

Effect of different S/D conditions on the
molecular weight distribution of
IgG solutions after SDR-chromatography

| Experimental conditions | | Before S/D addition and SDR | After 4.5 hs S/D Incubation and SDR |
|---|---|---|---|
| High S/D Concentration | Monomers | 96.17 | 99.28 |
| | Dimers | 3.78 | 0.62 |
| | Polymers | 0.04 | 0.21 |
| High Temperature | Monomers | 96.17 | 99.23 |
| | Dimers | 3.78 | 0.68 |
| | Polymers | 0.04 | 0.10 |

Example 2: Liquid Preparations Where S/D Were Removed

The same sample preparation procedure as in Example No. 1 was used, but this time the sample from which the solvent detergent (S/D) was removed by oil extraction and column chromatography was retrieved from a full production batch. The samples in which S/D was removed by chromatography on SDR were also retrieved from the same batch but at an earlier stage (after the S/D inactivation) and the chromatography was conducted at a smaller scale. To accelerate the filtration process the temperature of both solutions was elevated to 37° C. and both were adjusted to 45 mg/ml protein.

TABLE 4

Effect of C-18 resin as the SD removal procedure on
the flow rates and pressures during nano-filtration in Experiment 2

| | Pressure (psi) before filter | | Flow rate | Filtration volume |
|---|---|---|---|---|
| Measurement | 75N | 35N | (ml/min) | (ml) |
| 1 | 11 | 10 | 0.73 | 50 |
| 2 | 11 | 10 | 0.74 | 50 |
| 3 | 12 | 10 | 0.62 | 50 |
| 4 | 12 | 10 | 0.55 | 50 |
| 5 | 12 | 10 | 0.49 | 50 |
| 6 | 11.5 | 10 | 0.42 | 50 |
| 7 | 11 | 10 | 0.36 | 50 |

TABLE 5

Effect of SDR resin as the SD removal procedure on
the flow rates and pressures during nano-filtration in Experiment 2

| | Pressure (psi) before filter | | Flow rate | Filtration volume |
|---|---|---|---|---|
| Measurement | 75N | 35N | (ml/min) | (ml) |
| 1 | 11.5 | 10 | 1.25 | 50 |
| 2 | 11 | 10 | 1.08 | 50 |
| 3 | 11 | 10 | 1.00 | 50 |
| 4 | 11.5 | 10 | 0.96 | 50 |
| 5 | 11.5 | 10 | 0.89 | 50 |
| 6 | 11.5 | 10 | 0.84 | 50 |
| 7 | 11.5 | 10 | 0.83 | 50 |
| 8 | 11.5 | 10 | 0.78 | 50 |
| 9 | 12 | 10 | 0.74 | 50 |
| 10 | 11.5 | 10 | 0.66 | 50 |
| 11 | 11.5 | 10 | 0.6 | 17 |

Example 3: Effect of nanofiltration

Material was prepared as in Example 2. One was tested for viral removal by the use of 35N Planova filter. 45 mg/ml of IgG solution at pH 4.0 was spiked with HIV-1, PRV, BVDV, HAV or MVM. To obtain final concentration of more than $10^7$–$10^9$ PFU/ml all viruses were sedimented by ultracentrifugation and resuspended in water or serum free buffer in a small volume.

Because of the pH 4.0±0.1 of the starting material and the condition of filtration (37±C1° C.), the study of potential virucidal effect of this solution was evaluated at 35±1° C. on BVDV, before the study of nanofiltration with the Planova filter. The results obtained during the experiments showed a very low inactivation level (1.01 log) after 8 hours of incubation, in the stating material at pH=4.0. The same results were obtained with MVM and HAV. On the other hand at the same condition HIV and PRV after 6 hours of incubation, showed a 5.03 and 5.22 log reduction factor respectively.

The spiking experiments were carried out in duplicate according to the scale down conditions. Due to the early blocking of the 75N filter which occurred during the filtration of large viruses, a special set of three replaceable Planova 75N, 0.1 and 0.2 $\mu$M filter was set (FIG. 1). The pressure at the 35N filter was constantly adjusted to 0.7 bar. The filtrate was collected and the residual viruses were ultracentrifuged for maximal viral recovery.

The following table is attributed to the virus titer reduction factor of model viruses as a consequence of the nanofiltration throughout 35N and at the conditions mentioned above, e.g., incubation at 35±1° C. and pH=4.0, and the use of prefilters.

TABLE 6

Virus titer log reduction of various spiked model viruses

| Virus Name | Model for . . . | Reduction factor ($\log_{10}$) | Viral type |
|---|---|---|---|
| Human immunodeficiency virus type 1 (HIV-1) | HIV-1 and other Lentiviruses | >5.25(>5.18, >5.31) | Enveloped RNA |
| Pseudorabies virus (PRV) | Hepatitis B | >5.58 | Enveloped DNA |
| Minute Virus of mice (MVM) | Parvovirus B-19 | 1.71(1.91, 1.51 | Non enveloped DNA |
| Bovine Viral Diarrhea virus (BVDV) | Hepatitis C | 4.62(4.91, 4.34) | Enveloped RNA |
| Hepatitis A (HAV) | Hepatitis A | >8.68 | Non-Enveloped RNA |

This specific step neither reduces the protein concentration nor changes the characteristics of the immunoglobulin, e.g., the Fe function, the Anti-Complementary Activity (ACA) and the integrity of the molecule as tested by HPLC have been preserved.

Example 4: Nanofiltration After S/D Removal In a Fibrinogen Preparation

A resuspended cryo-precipitate at pH 7.5 after Alhydrogel adsorption to deplete vitamin K dependent proteases were subjected to viral inactivation using a Solvent/Detergent (S/D) mixture of 1% TnBP and 1% Triton X-100™. The mixture was incubated at 30° C. for 4 hrs. Then the S/D mixture was removed either by castor oil followed by chromatography on a Bulk C-18 resin from Waters or a chromatography on a Biosepra's SDR HyperD™ resin without prior oil extraction. Both samples were then filtered through the same filtration process as in Example 1 and the flow rates every 10 ml were monitored. The results are presented in Tables 6 and 7.

TABLE 7

Effect of C-18 resin as the SD removal procedure on
the flow rates and pressures during nano-filtration in Example 4

| Measurement | Pressure (psi) before filter | | Flow rate | Filtration volume |
| --- | --- | --- | --- | --- |
| | 75N | 35N | (ml/min) | (ml) |
| 1 | 12.5 | 10 | 5 | 10 |
| 2 | 12.5 | 10 | 4.0 | 10 |
| 3 | 12.5 | 10 | 3.4 | 10 |
| 4 | 12 | 10 | 2.3 | 5 |

TABLE 8

Effect of C-18 resin as the SD removal procedure on
the flow rates and pressures during nano-filtration in Experiment 4

| Measurement | Pressure (psi) before filter | | Flow rate | Filtration volume |
| --- | --- | --- | --- | --- |
| | 75N | 35N | (ml/min) | (ml) |
| 1 | 11.5 | 10 | 4.9 | 10 |
| 2 | 12 | 10 | 4.8 | 10 |
| 3 | 12 | 10 | 4.7 | 10 |
| 4 | 12 | 10 | 4.8 | 10 |
| 5 | 12 | 10 | 4.1 | 10 |
| 6 | 12.5 | 11 | 2.4 | 10 |
| 7 | 12 | 11 | 2.0 | 5 |

As shown in Tables 6 and 7 even though the initial flow rates were similar on both resins, the flow rate decreased faster when using the combination of oil extraction (C-18) and consequently, the filtration volume was lower when using the C-18 resin (35 ml) in comparison with the filtration volume when using SDR (65 ml).

What is claimed is:

1. A method for the inactivation of viruses present in a biological liquid preparation comprising the steps of:

(a) treating the biological liquid preparation with a solvent-detergent combination, at concentrations and under conditions which are sufficient to inactivate lipid-coated viruses;

(b) removing the solvent-detergent combination from the liquid preparation by passing the liquid preparation obtained in (a) on a chromatographic packing composed of silica beads which pore volume is filled with three-dimensional cross-linked hydrophobic acrylic polymer; and (c) passing the liquid product of step (b) through a filter having a pore size from about 15 nm to about 70 nm.

2. A method according to claim 1, wherein after step (a) comes a step (a1) comprising:

(a1) extracting the solvent-detergent combination by a hydrophobic moiety.

3. A method according to claim 2, wherein the hydrophobic moiety is a biologically compatible vegetable oil.

4. A method according to claim 1, wherein the solvent-detergent combination containing at least one of the agents selected from the group consisting of: TnBP, octylphenol ethyleneoxide condensate, polyoxyethylene sorbitan monooleate and sodium cholate.

5. A method according to claim 1, wherein the liquid preparation is obtained from human plasma.

6. A method according to claim 1, wherein the liquid preparation originates from a precipitate of human plasma.

7. A method according to claim 6, wherein the precipitate is a cryoprecipitate.

8. A method according to claim 6, wherein the precipitate contains immunoglobulins.

9. A method according to claim 1, wherein the liquid preparation is a preparation obtained by a method comprising:

(i) obtaining an immunoglobulin-containing precipitate from plasma;

(ii) resuspending said precipitate in water;

(iii) adjusting the pH of the preparation obtained in step (b) to a pH below 5; and (iv) ultrafiltering/diafiltering the preparation obtained in step (c) using membrane filters to give a desired protein concentration.

10. A method according to claim 6, where the pH of step (c) is adjusted to a pH below 5.

* * * * *